United States Patent [19]
McPhee

[11] Patent Number: 5,199,948
[45] Date of Patent: Apr. 6, 1993

[54] NEEDLELESS VALVE

[75] Inventor: Charles J. McPhee, Huntington Beach, Calif.

[73] Assignee: McGaw, Inc., Irvine, Calif.

[21] Appl. No.: 694,637

[22] Filed: May 2, 1991

[51] Int. Cl.⁵ .............................................. A61M 37/00
[52] U.S. Cl. ........................................ 604/86; 604/88; 604/167; 604/411
[58] Field of Search ............... 604/167, 169, 256, 247, 604/411, 905, 86, 88, 170, 412, 201, 202; 251/149.1; 137/844, 847

[56] References Cited

U.S. PATENT DOCUMENTS

| | | | |
|---|---|---|---|
| 3,577,992 | 5/1971 | Merry et al. | 128/349 |
| 3,695,478 | 10/1972 | Sie et al. | 604/201 |
| 3,900,028 | 8/1975 | McPhee | 128/272 |
| 3,994,293 | 11/1976 | Ferro . | |
| 4,177,814 | 12/1979 | Knepshield et al. | 604/167 |
| 4,197,848 | 5/1980 | Garrett et al. | 128/247 |
| 4,416,661 | 11/1983 | Norman et al. | 604/86 |
| 4,496,348 | 1/1985 | Genese et al. | 604/169 |
| 4,559,043 | 12/1985 | Whitehouse et al. | 604/201 |
| 4,610,665 | 9/1986 | Matsumoto et al. | 604/167 |
| 4,662,878 | 5/1987 | Lindmayer | 604/411 |
| 4,809,679 | 3/1989 | Shimonaka et al. | 604/167 |
| 4,857,062 | 8/1989 | Russell | 604/167 |
| 4,874,377 | 10/1989 | Newgard et al. | 604/167 |
| 4,895,565 | 1/1990 | Hillstead | 604/167 |
| 4,915,687 | 4/1990 | Sivert . | |
| 5,009,391 | 4/1991 | Steigerwald | 604/167 |
| 5,059,186 | 10/1991 | Yamamoto et al. | 604/265 |
| 5,071,413 | 12/1991 | Utterberg | 604/411 |

FOREIGN PATENT DOCUMENTS

| | | | |
|---|---|---|---|
| 964544 | 3/1975 | Canada | 128/127.1 |
| 232074 | 8/1987 | European Pat. Off. . | |
| 0344907 | 12/1989 | European Pat. Off. . | |
| WO89/06553 | 7/1989 | PCT Int'l Appl. . | |
| 2143134 | 2/1985 | United Kingdom . | |

OTHER PUBLICATIONS

PCT Publication No. WO 90/11103.

*Primary Examiner*—Cary E. O'Connor
*Attorney, Agent, or Firm*—Christie, Parker & Hale

[57] ABSTRACT

An injection set with a slit septum held in place in the inlet of a housing by a cap affixed to the inlet. A concave end of the septum is exposed through an aperture in the cap, and a peripheral flange portion of the septum is squeezed between the housing inlet and the cap, causing the septum's concave end to bulge and flatten, thus improving the sealing of the septum's slit. Extending through the septum slit is a drug transfer spike having a ball-shaped tip sharp enough to penetrate the diaphragm of a drug vial but not so sharp as to puncture the skin of a user.

27 Claims, 9 Drawing Sheets

NEEDLELESS VALVE

FIELD OF THE INVENTION

The present invention relates generally to medical systems for administering fluids to a patient, and more particularly to pre-slit injection sites and a needle replacement called a "drug transfer spike," for use in such systems.

BACKGROUND OF THE INVENTION

An integral part of modern medical care is the administration of fluids to a patient through an entry point made in a vein of the patient. A catheter is inserted in the vein and an administration set, comprised principally of flexible tubing, connects the catheter to a source of fluid. Alternatively, medication may be injected into the catheter from a syringe through a drug transfer spike attached to the syringe and a connector having a sealable inlet penetrable by the tip of the drug transfer spike. Y connectors are customarily included in an administration set to allow fluids from two or more sources to flow through a common tube to the patient. Such Y connectors also have a sealable inlet through which the tip of a piercing member can penetrate. The branch containing the sealable inlet in these and other related medical connecting devices is commonly referred to as an "injection site". Injection sites usually feature an elastomeric plug, called a "septum", to form the seal.

One type of injection site includes a slit extending through the septum which permits the injection site to be penetrated by a blunt piercing member. Such pre-slit septums reduce accidental punctures which might result from the use of a sharp-tipped cannula.

One object of the present invention is to minimize leakage through the slit of a pre-slit septum in an injection site during or after being penetrated by a cannula.

When medication is to be administered from a syringe through a drug transfer spike inserted into a connector through its septum, the syringe is first filled from a drug vial through the same drug transfer spike by inserting the spike through the diaphragm that closes the inlet of the drug vial. Since drug vial diaphragms are not pre-slit, the drug transfer spike must be sharp enough to penetrate them. To prevent user injury and contamination, drug transfer spikes should not be sharp enough to easily pierce skin. It is therefore a related object of the invention to provide a drug transfer spike having a piercing member which is sharp enough to penetrate a drug vial diaphragm but blunt enough to prevent coring or abrasion of the septum and also to avoid puncturing a user's skin. An alternative related object of the invention is to provide a syringe with an integral piercing member having the piercing attributes of the aforesaid drug transfer spike.

SUMMARY OF THE INVENTION

These and other objects of the invention are achieved by an injection site which comprises a housing having an inlet, a septum having a cylindrical body and means for securing the septum to the housing at the inlet. The septum's cylindrical body includes first and second ends, a peripheral portion, a concave surface in one or both end(s), and a slit which extends axially from the concave surface in the first end at least substantially into the septum. The septum's peripheral portion is compressed at the inlet while its central region is free to move, causing the septum's concave surface to bulge. This causes the concave surface to flatten and the seal between opposite faces of the slit to be improved. Alternatively, an improved seal may be achieved without the concave surface(s) in the septum end(s) merely by the axial compression of the septum's peripheral portion and the resultant radially-inwardly-directed forces. There are also provided, particularly for use with the injection site, a syringe and a drug transfer spike having a piercing member extending through the septum's slit and terminating in a ball-shaped tip, resulting in a device which is sharp enough to penetrate a drug vial membrane but blunt enough to prevent injury to the user and coring or abrasion of the injection site septum.

BRIEF DESCRIPTION OF THE DRAWINGS

These features and advantages of the invention, as well as other features and advantages of the invention, will be more apparent from a reading of the claims and of the detailed description of the invention in conjunction with the drawings described below.

DETAILED DESCRIPTION

Figure 1:
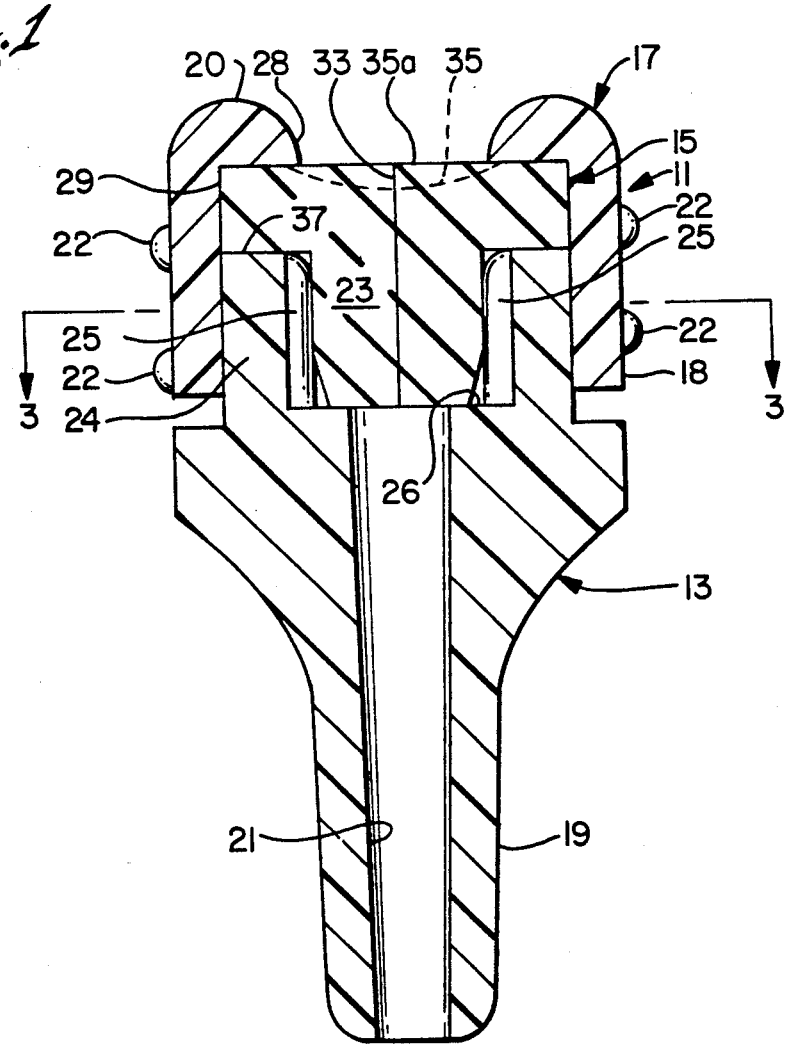
FIG. 1 is a cross-section through an injection site constructed in accordance with the present invention.
Figure 2:
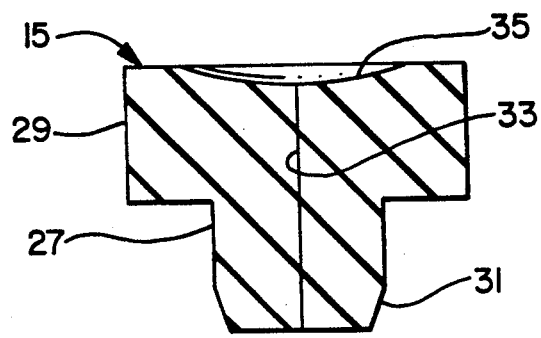
FIG. 2 is a cross-section through the septum of the injection site of FIG. 1 removed from the injection site.
Figure 3:
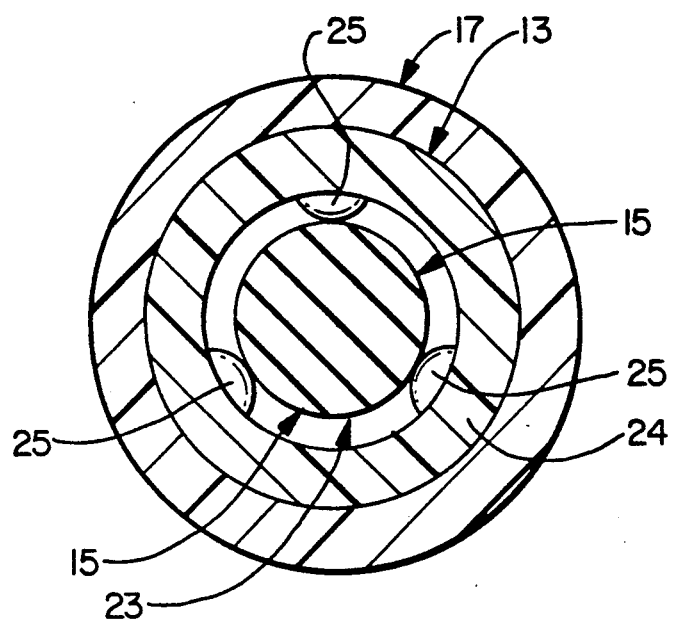
FIG. 3 is a cross-section along lines 3—3 of FIG. 1 showing the body of the septum centered in the inlet of the injection site housing.

Injection site 11, adapted to be inserted into a receptacle such as that of a catheter and to receive a piercing member such as that of a drug transfer spike, is illustrated in FIGS. 1-3. It comprises a housing 13, septum 15, and retaining cap 17. The housing 13 and cap 17 may both be formed of a plastic such as that identified by the trademark EKTAR, available from Eastman-Kodak Co., or an acrylic or ABS. Of these, EKTAR is presently preferred. The cap 17 comprises an annular head 20 from which there extends a skirt 18 around which wind one or more thread(s) 22. Centered in the cap head 20 is an access aperture 28. The septum 15 is preferably formed of natural rubber. The housing 13 has an extended tapered stem 19 with a tapered axial passage 21. Communicating with the tapered passage 21 is a recess 23 defined by a cylindrical wall 24 from which there extend a plurality of centering ribs 25. The recess 23 terminates in a floor 26 in whose center is an opening to the axial passage 21, the floor 26 being formed by the shoulder between the recess 23 and the passage 21.

The septum 15 is shown in its relaxed form prior to being installed in the housing 13 in FIG. 2. T-shaped in cross-section, it has a body 27 with a peripheral flange portion 29 and terminates in a tapered tip 31 at one end. The septum 15 is formed with a centrally-disposed concave surface 35 in the other end of the septum body 27. A slit 33 extends from the concave surface 35 through the septum body 27.

When the injection site 11 is assembled, the tapered end of the septum body 27 extends into the housing recess 23, being guided and centered by the ribs 25. The septum's flange portion 29 rests on the rim 37 of the wall 24 which forms the recess 23. The retaining cap 17 fits snugly over the exterior of the wall 24 and is secured thereto by appropriate means, such as sonic bonding, in such a manner as to compress the septum's flange portion 29 between the retainer cap head 20 and the rim 37. Preferably, the inside diameter of the cap skirt 18 is no greater than the outside diameter of the septum's flange portion 29, and indeed it is particularly preferred that there be an interference fit between the two. As a result, compression of the flange portion 29 between the rim 37 and the cap 17 forces the flange portion to bulge so as to move its concave surface 35 toward a substantially flat configuration, as shown in FIG. 1. This configuration results in increased compression of the slit 33 at its intersection with the concave surface 35, providing an improved seal. Increased compression of the slit 33 results from the portions of the concave surface 35, on opposite sides of the slit 33, moving toward each other as they swing from their concave position, shown in FIG. 2, to their compressed, flat position 35a, shown in FIG. 1. Although not essential, the tapered end 31 of the septum body 27 contacts the recess floor 26 and is pressed against it by the action of the retaining cap 17.

By virtue of the centering ribs 25, the septum body 27 becomes centered in the inlet recess 23 so that it is spaced from its wall 24 prior to securing of the retaining cap 17 on the housing inlet. When a piercing member is inserted through the septum's slit 33, the septum body bulges into the interstices between the wall 24 and the ribs 25.

Figure 4:
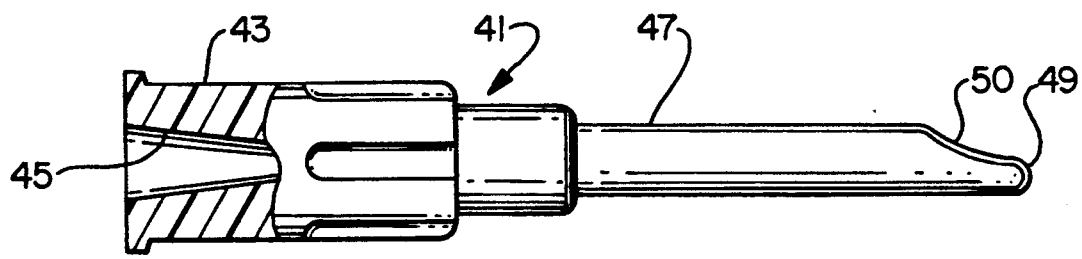
FIG. 4 is a side view, partially broken away, of a drug transfer spike intended particularly for use with the injection site of FIG. 1.
Figure 5:
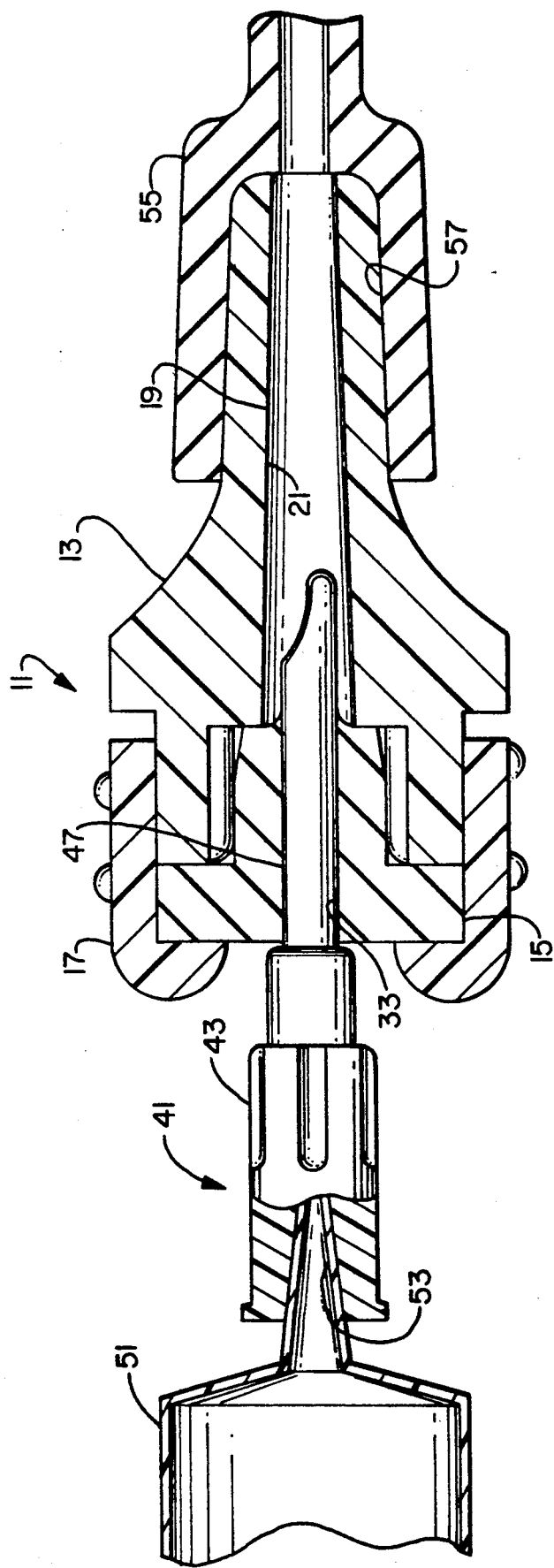
FIG. 5 is a side view, partially broken away, of the drug transfer spike of FIG. 4 assembled on the end of a syringe and the injection site inserted into the receptacle of a catheter, the syringe being placed in communication with the catheter through insertion of the drug transfer spike into the injection site.
Figure 10:
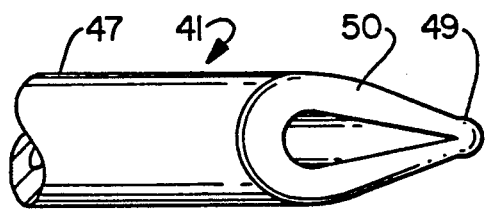
FIG. 10 is an enlarged side view of a terminal portion of the drug transfer spike of FIG. 4.
Figure 11:
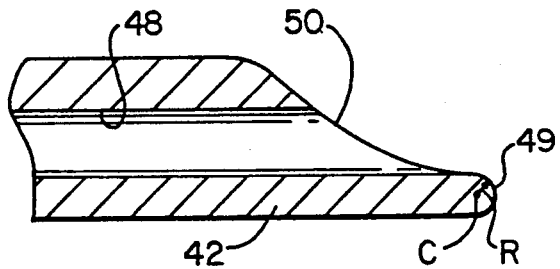
FIG. 11 is a cross-sectional view of the terminal portion of the drug transfer spike illustrated in FIG. 10.
Figure 12:
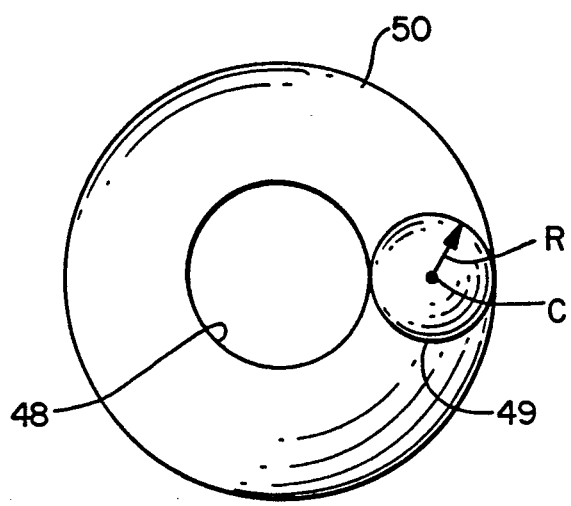
FIG. 12 is an end view of the drug transfer spike terminal portion illustrated in FIGS. 10 and 11.

A drug transfer device, commonly referred to as a "drug transfer spike" 41, adapted to be inserted in the injection site 11, is illustrated in FIG. 4. It includes a knurled cylindrical receptacle 43 having a tapered axial passage 45 and supporting a piercing member 47 terminating in a tip 49. A lumen 48 (shown in FIG. 11) extends through the piercing member 47 to the tapered passage 45, establishing communication therewith. The tapered axial passage 45 is adapted to receive the tapered tip 53 of a syringe 51, as shown in FIG. 5, which also shows the piercing member 47 inserted through the septum 15 into the injection site 11 and the tapered stem 19 of the injection site housing 13 inserted into the receptacle 57 of a catheter 55. The entire drug transfer spike 41 may be formed as a single member of the same material as the housing 13. In accordance with the invention, the tip of the piercing member 47 is sufficiently sharp to penetrate not only the slit 33 of the septum 15 but also to penetrate the membrane of a drug vial (not shown), yet is not so sharp as to break the skin of a user. The terminal portion of the piercing member 47 is best seen in FIGS. 10 and 11. The tip 49 is formed of the end of the wall 42 of the drug transfer spike 41 by virtue of the slanted, tapered scarf 50 extending across opposite halves of the annular wall 42. In accordance with the invention, the piercing member tip 49 is ball-shaped, with a center typically midway between the inner and outer surfaces of the annular wall 42 and defined by a radius R anchored on that center point C and being of a size substantially one-half the thickness of the wall 42 so that the ball-shaped tip 49 blends into the end surface 50, as shown in FIGS. 10 and 11. With a suitable drug transfer wall thickness being 0.030 inch, the resulting tip 49 will be 0.030 inch in diameter, presenting a puncturing surface projection of 0.000707-inch square. A spike tip of such size is believed optimal for reconciling the need for safety with the ability to penetrate conventional drug vial membranes.

Figure 13:
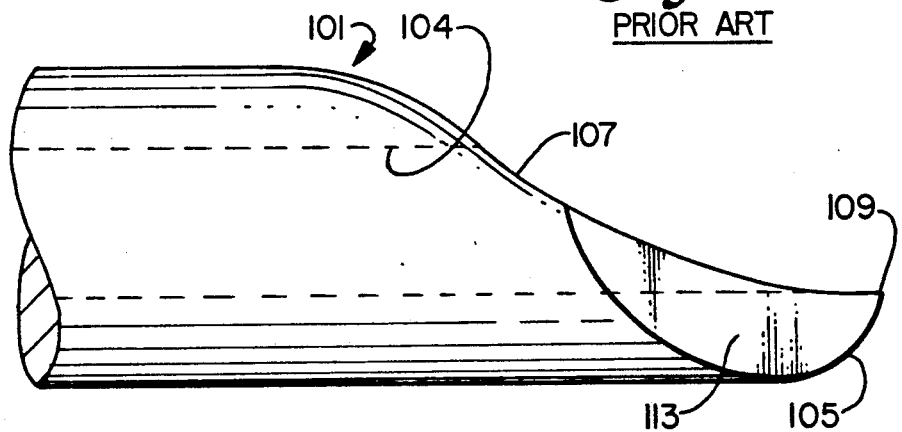
FIG. 13 is a side view of the terminal portion of a typical IV spike.
Figure 14:
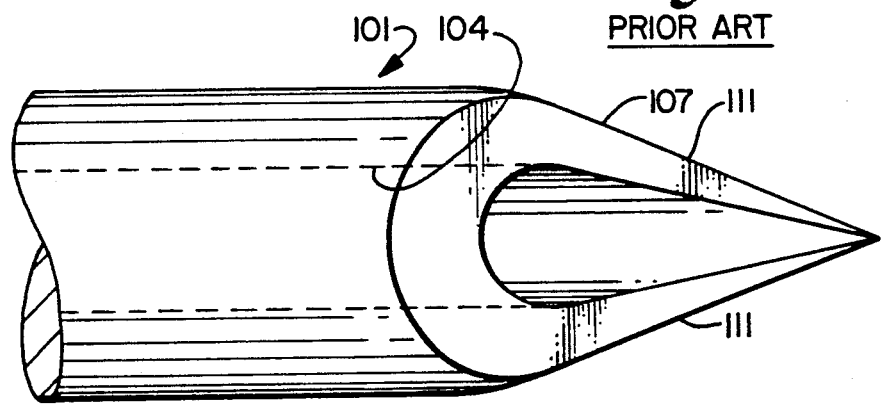
FIG. 14 is a plan view of the IV spike illustrated in FIG. 13.
Figure 15:
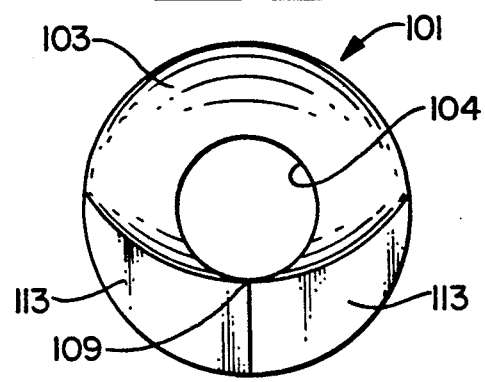
FIG. 15 is an end view of the IV spike of FIG. 13.

The foregoing configuration is in contrast to the typical IV spike 101 illustrated in FIGS. 13-15. The spike 101 also has an annular wall 103 having an axial passage 104 and terminating in a tip 109. However, the tip 109 is not ball-shaped, but has a sharp surface where its part-hemispherical surface 105 intersects the scarf 107 of the spike 101. Typically, the tip 109 is formed by removing a portion of the wall 103 not only to form the scarf 107, best seen in FIG. 13, but also along the lines 111 to generate opposed surfaces 113, bringing the wall 103 to a relatively-sharp tip 109 at the intersection of the surfaces 104, 105, and 113.

Figure 6:
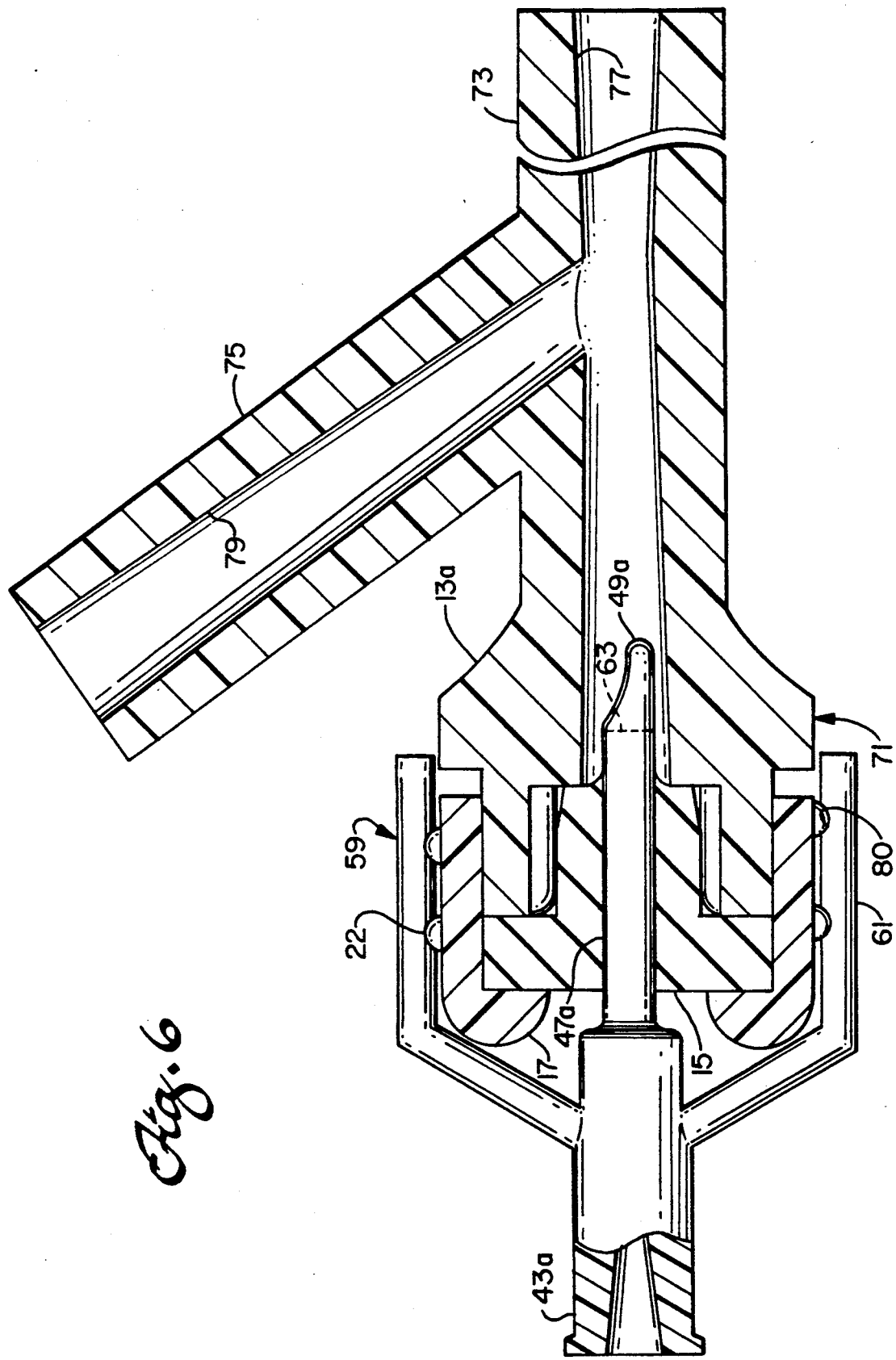
FIG. 6 is a side view, partially broken away, of a Y connector featuring an injection site similar to that illustrated in FIG. 1 and penetrated by the cannula of a threaded connector.

Illustrated in FIG. 6 is a Y connector, commonly called a "Y site", 71 incorporating an injection site of the present invention. The Y site 71 comprises a body 13a, which may be identical to the body 13 illustrated in FIG. 1 but with a tapered main branch, or stem, 73 from which there extends a side branch 75. Axial passages 77 and 79 extend through the branches 73 and 75 respectively and are shown tapered toward the point where they intersect to accommodate plastic tubing which may be inserted into the housing. The Y site 71 is engaged by a threaded connector 59 having a hub 43a and piercing member 47a substantially similar to the similarly-labeled elements in FIG. 4 but with an internally-threaded cap 61 extending from the hub 43a. Internal threads 80 of the cap 61 are adapted to engage the external threads 22 of the retaining cap 17, which may be essentially like that illustrated in FIG. 1. The piercing member 47a may have a semi-sharp tip, such as that described with reference to FIG. 4, or it may have a blunt tip 63, shown in dashed lines. The latter alternative is acceptable, since the threaded connector will not usually be expected to be able to penetrate an unslit septum or drug vial diaphragm.

Figure 7:
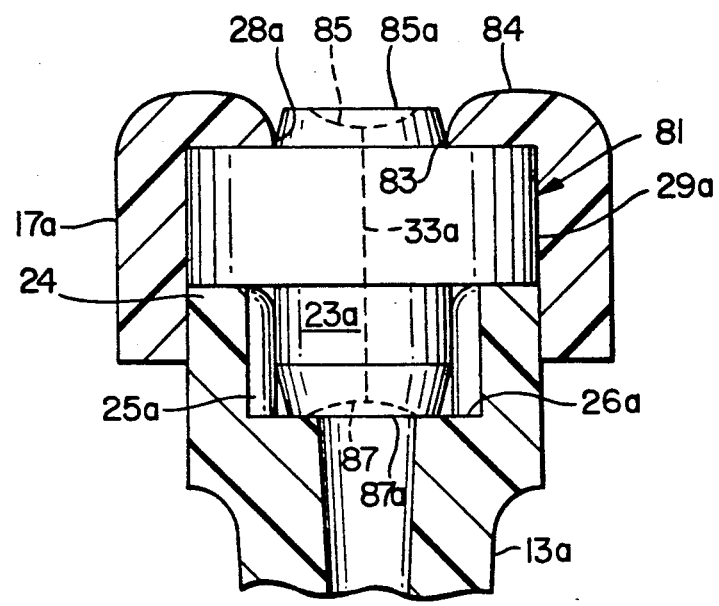
FIG. 7 illustrates a modified embodiment of the injection site similar to that illustrated in FIG. 1 but with a septum which is cross-shaped in cross-section and which is provided with a dimple at both ends.
Figure 8:
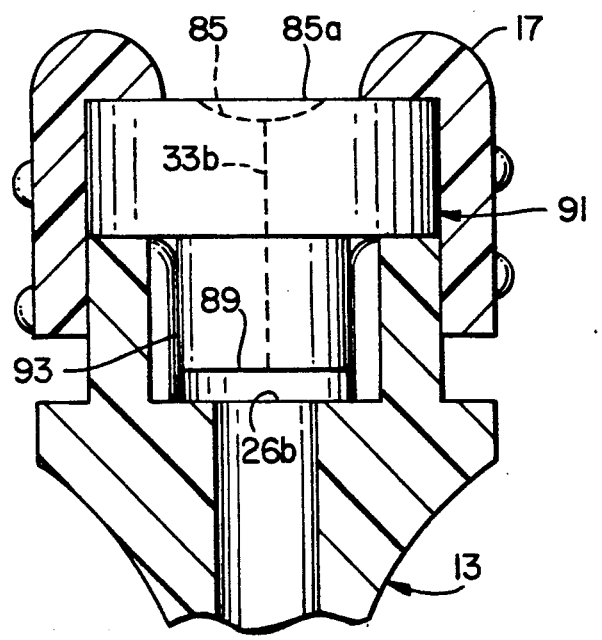
FIG. 8 is a second modified embodiment of the injection site of FIG. 1, wherein the body of the septum is spaced from the floor of the housing inlet in which the septum is positioned.

Several alternative configurations of the pre-slit septum 15 will occur to those skilled in the art. Two of them are illustrated in FIGS. 7 and 8. In the alternative embodiment of FIG. 7, a septum 81 is shown featuring a T-shaped cross-section. The modified septum 81 differs from that illustrated in FIGS. 1-3 in two principal respects. First, the end 83 of the septum body opposite that which enters the housing recess 23a extends beyond the septum's flange portion 29a and extends into the cap head's central aperture 28a so that the septum body's concave surface 85 rises substantially to the level of the cap head's exterior surface 84 when the cap 17a is secured to the inlet of the housing 13a.

A second point of departure is the addition of a second concave surface 87 to the opposite end of the septum 81 to provide an improved seal there, also. For sake of clarity, the concave surfaces 85 and 87 of the embodiment of FIG. 7 are shown in dashed lines, since those surfaces will be concave to the extent shown only prior to attachment of the retaining cap 17a to the housing inlet. Thereafter, as previously described, the concave surfaces 85 and 87 will bulge out to their relatively flat configuration, shown by the solid lines 85a and 87a. Partially contributing to the flattening of the concave surface 87 is the forcing of that end against the ledge 26a, which forms the floor of the recess 23a in FIG. 7. Slit 33a, extending between the surfaces 85 and 87, is incrementally compressed at its intersection with those surfaces due to their flattening.

A second alternative embodiment of the injection site of the present invention is shown in FIG. 8. Its septum 91 is essentially similar to that shown in FIGS. 1-3, with the exception that the septum body 93 is not tapered at its end and in that it stops short of the recess floor 26b. Consequently, when a piercing member is inserted through the septum's slit 33b, the septum body 93 has room to expand toward the recess floor 26b, as well as into the interstices between the ribs 25a and the wall 24a.

Figure 9:
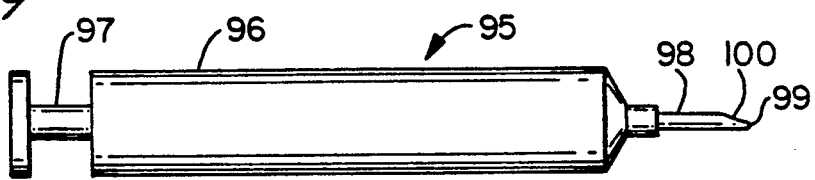
FIG. 9 is a side view of a syringe with integral drug transfer spike intended for use particularly with the injection site of FIG. 1.

FIG. 9 illustrates a syringe 95 comprising a barrel 96 in which a plunger 97 is slidably disposed through a proximal end of the barrel. The barrel 96 may be formed of the same or other suitable material as the drug transfer spike 41 of FIG. 4. The distal end of the barrel terminates in an integral piercing member 98 having a tapered end face 100 terminating in a tip 99 whose sharpness meets the same piercing criteria as does the tip 49 of the drug transfer spike 41. Accordingly, the syringe 95 is adapted to withdraw medication from a drug vial having a closure diaphragm which needs to be penetrated. In keeping with the invention, the syringe 95, although capable of piercing a drug vial diaphragm, is safe to use, since its tip 99 is not sufficiently sharp to pierce the skin of a user.

Figure 16:
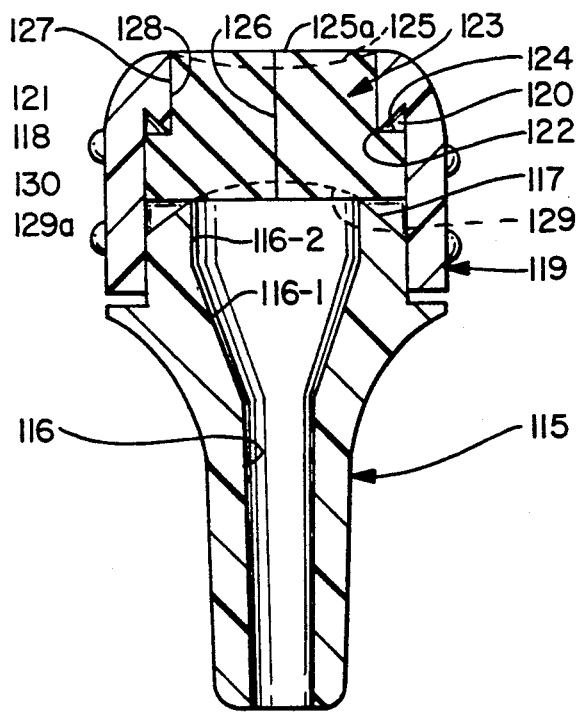
FIG. 16 illustrates a third modified embodiment of the injection site of FIG. 1 having a concave surface in its opposite ends and a flange located between tapered annular surfaces of a cap and a housing, to provide for axial expansion of the septum's flange.

A third, and presently preferred, alternative embodiment of the injection site of the present invention is illustrated in FIG. 16. It comprises a housing 115 which is essentially similar to the housing 13 of FIG. 1, but with the following significant differences. The housing 115 has an axial passage 116 with a tapered transitional region 116-1 and a wide throat region 116-2. The front end of the housing 115 is formed by a tapered annular surface 117 which, together with the throat portion 116-2, forms an annular ridge 118. A modified cap 119 is attached to the front end of the housing 115 over its inlet in a manner similar to that employed to attach the corresponding cap 17 in FIG. 1. Disposed between the modified cap 119 and the modified housing 115 is a modified septum 123. The septum 123 includes a flange 124 having a bottom surface seated on the annular ridge 118. Extending away from the housing 115 is a reduced body portion 127 of the septum, which extends into a circular opening 128 in the front end of the cap 119. The reduced body portion 127 of the septum terminates in a concave surface 125. The cap opening 128 is formed by a ledge having a tapered annular surface 121 terminating in an annular ridge 122. The annular space 120 formed between the septum flange 124 and the tapered surface 121 provides a space for expansion of the septum 123 when a piercing member is inserted through the slit 126, which extends between opposite concave surfaces 125 and 129 of the septum. A similar annular space 130 is formed between the bottom surface of the septum 123 and the annular surface 117 of the housing 115. In keeping with the invention, the cap 119 is attached, such as by sonic bonding, to the housing 115 so that the septum's flange 124 is compressed between the annular ridges 122 and 118 of the cap and housing 119 and 115, respectively. As a result, the concave surfaces 125 and 129 are caused to bulge axially to substantially-flat configurations 125a and 129a. Advantageously, the external concave surface 125 becomes substantially flush with the front surface of the cap 119.

Figure 17:
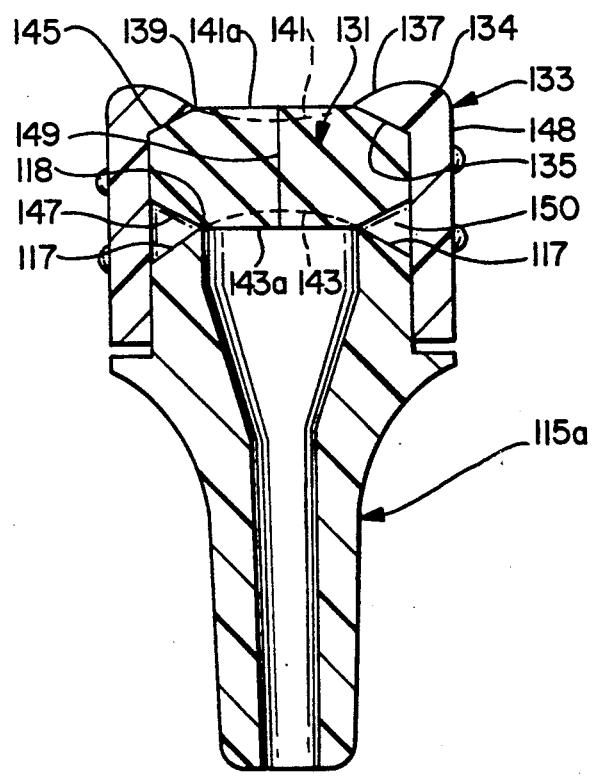
FIG. 17. is a fourth modified embodiment of the injection site of FIG. 1, wherein the septum, instead of a peripheral flange like that of FIG. 1, has tapered surfaces around its opposite ends, each of which has a centrally-disposed annular surface which extends between a respective one of the peripheral tapered surfaces.

A fourth alternative embodiment of the injection site of the present invention is illustrated in FIG. 17. Its housing 115a may be identical to the housing 115 of FIG. 16. Attached to the housing 115a is a cap 133, and held between the housing 115a and the cap 133 is a septum 131. The cap 133 has an end wall 134 with a central opening defined by a peripheral ridge 139, formed by the intersection of inner and outer sloped annular surfaces 135 and 137. The septum 131 is essentially puck-shaped, with outer and inner concave surfaces 141 and 143. The inner concave surface 143 is surrounded by a tapered annular surface 147, and the outer concave surface 141 is similarly surrounded by a tapered annular surface 145. The tapered annular surfaces 145 and 147 terminate in a peripheral cylindrical surface 148. A slit 149 extends between the concave surfaces 141 and 143. The tapered annular surface 147, in combination with the tapered surface 117 of the housing 115a, provides a slightly-larger expansion space 150 than the expansion space 130 of FIG. 16. The cap and septum 133 and 131 combine to provide an almost-flush end face formed by the head of the cap 133 and the concave septum surface 141.

The insertion site of FIG. 17 operates on the same principle as all of the other embodiments thereof, with the septum 131 being compressed between the cap 133 and the housing 115a so as to cause the concave surfaces 141 and 143 to bulge to substantially-flat configurations 141a and 143a.

Figure 18:
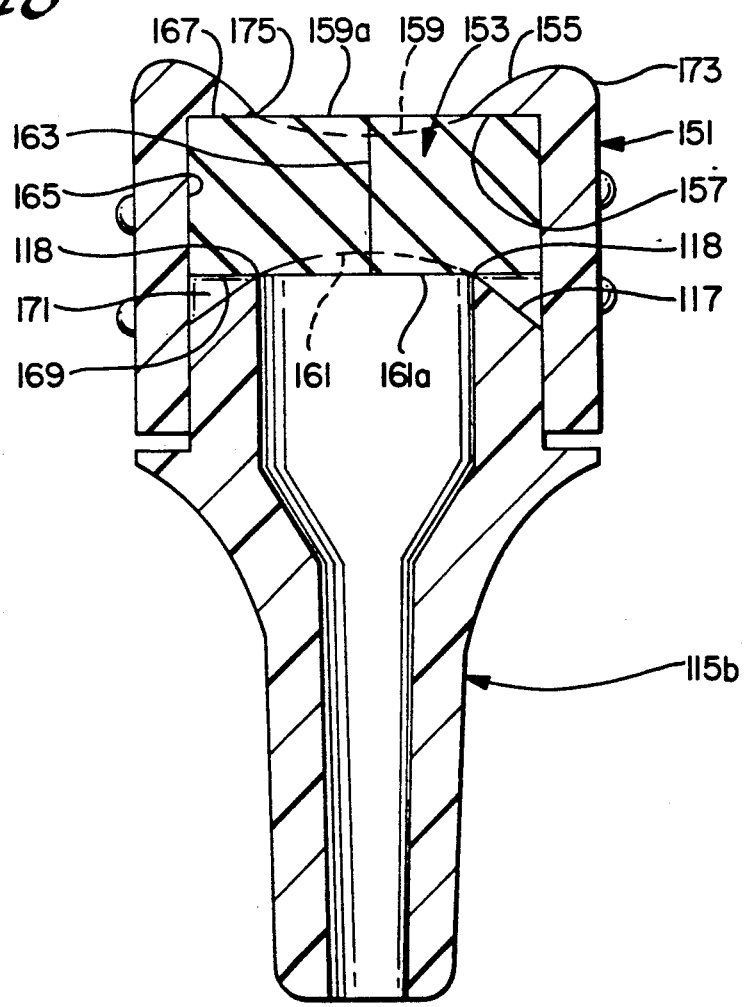
FIG. 18 is a fifth modified embodiment of the injection site of FIG. 1, wherein the septum is essentially puck-shaped, and the housing has a tapered surface facing one end of the septum to provide for axial expansion of the septum's peripheral portion.

A fifth alternative embodiment of the injection site of the present invention is shown in FIG. 18. Its housing 115b may be similar to the corresponding housings 115 and 115a of FIGS. 16 and 17. The injection site additionally includes a septum 153 and cap 151, each of which is configured differently than the septum and cap of the other embodiments. The septum 153 is essentially puck-shaped, with flat outer and inner end faces respectively having centrally-disposed concave surfaces 159 and 161 connected by a slit 163. A peripheral cylindrical face 165 extends between the opposite faces 167 and 169 of the septum. Since the inner face 169 of the septum 153 is configured essentially like that of the septum 123 of FIG. 16, it forms, in combination with the housing 115b, an expansion space 171 similar to the expansion space 130 of FIG. 16. The cap 151 has a head 173 with a central opening formed by an annular ridge 175 created by the intersection of flat annular inner surface 157 and the tapered annular outer end surface 155 of the cap head 173. The outer concave surface 159 is disposed substantially in registry with the opening in the cap head 173, and the inner concave surface 161 is similarly substantially in alignment with the opening defined by the annular ridge 118 of the housing 115b. As in the cases of the previous embodiments, the cap 151 is so attached to the housing 115b that the septum 153 is compressed between them so as to cause its opposed concave surfaces 159 and 161 to bulge into substantially-flat configurations 159a and 161a, respectively.

It will be noted that all three of the injection sites described with reference to FIGS. 16-18 feature a septum which is seated on the annular rim of the inlet of their housing, rather than extending into the inlet, as was the case with the first three embodiments described with reference to FIGS. 1, 7, and 8, resulting in differently-configured septums and caps. In addition to illustrating differently-configured septums and retainer caps, the three alternative embodiments of FIGS. 16-18 also illustrate that, in lieu of the radially-extending ribs 25 of FIG. 1, tapered annular surfaces on one or both of the septum and housing may provide the necessary expansion space for the septum when it receives a piercing member. All six embodiments share a common feature: A portion of the septum which interfaces with the skirt of the retainer cap fits snugly in the cap's skirt, preferably with an interference fit, so that, as the cap is secured to the housing, the septum is squeezed between the housing and the cap and is thereby forced to expand axially, causing its concave end surfaces to bulge until they are nearly flat. It will be noted that, in all three embodiments of FIGS. 16-18, the housing 115, 115a, and 115b has an inlet which terminates in a wedge-shaped rim on which the septum of the respective injection site is seated. This is in contrast to the first three embodiments, wherein the housing is provided with a flat-floored recess, and the septum body extends into the recess.

Figure 19:
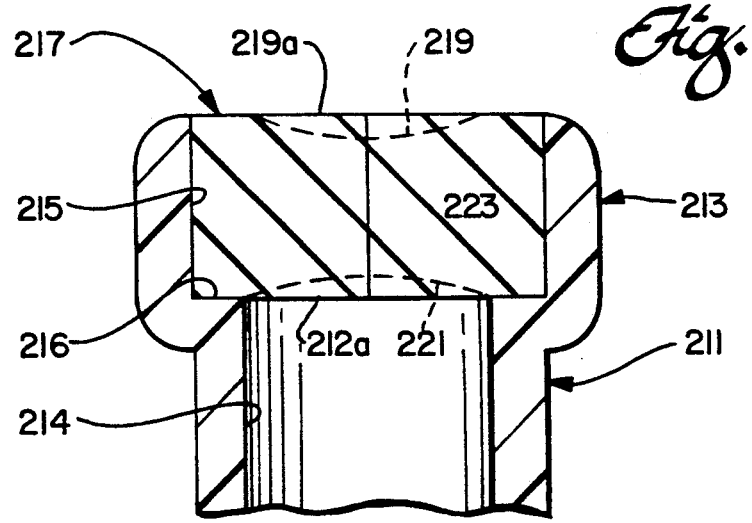
FIG. 19 is a sixth modified embodiment of the injection site of FIG. 1, wherein the septum is retained in the housing by bonding rather than by a retaining cap.

A sixth alternative embodiment is illustrated in FIG. 19. It comprises a housing 211 terminating in an enlarged inlet portion 213 and a puck-shaped septum 217 configured like its counterpart in FIG. 18 residing in the housing inlet 213. Only the terminal portion of the housing 211 is shown, since its distal end may be identical to the housings shown in the other figures, such as in FIG. 18. An axial passage 214 through the housing 211 opens into an enlarged inlet 215, the transition between the two forming the floor 216 of the inlet whose side is the cylindrical wall 215. In keeping with the invention, the septum 217 is formed in place in the inlet portion 213. Preferably, by means of a pair of opposite mandrels (not shown), an enclosed space is defined within the inlet portion 213, and an elastomeric plastic resin is injected under pressure through an orifice in one of the mandrels into the enclosed space. The opposed mandrels have dome-shaped ends so as to create opposed concave surfaces 219 and 221. The elastomeric plastic resin should be of a material which readily bonds, upon cooling, to the wall 215 and floor 216 of the housing inlet 213. Once the resin has cooled and bonded to the housing inlet 213 and the mandrels are removed, the peripheral portion of the septum 217 is anchored to the wall and floor 215 and 216 of the inlet, while the opposed concave centrally-disposed portions 219 and 221 of the septum 217 are free to move. As a result of the residual pressure, now relieved by removal of the mandrels, they will bulge to their positions 219a and 221a, respectively. Conversely, the rim, or peripheral portion of the septum 217, remains compressed due to the bond between that portion and the housing inlet wall 215. As before, a slit 223 extends between opposite concave surfaces 219 and 221.

Thus, it may be seen that, as in the case of the previous five embodiments, means are provided for securing the septum to the housing at the inlet, with a peripheral portion of the septum body being compressed so as to cause the concave surfaces to bulge. What sets the sixth embodiment apart from the first five, is that, instead of a retaining cap securing the septum to the housing, so as to compress the septum between the housing and the cap, the septum is formed under pressure in the housing, and its rim is kept compressed, by means of a bond between the housing and the peripheral portion of the septum.

All of the disclosed septum embodiments incorporate a slit which extends entirely through the septum, and this is presently preferred. It will be understood, however, that the invention may also be implemented with septums whose slits extend substantially (at least halfway) into the septum; that is, from its concave end through which a piercing member is inserted, whereby the septum is ruptured by that member so as to extend the slit to the opposite end of the septum nearest the floor of the housing inlet. Even though the inner end of the slit terminates in a ruptured line, the seal effected at that ruptured line will be improved by the initially-concave surface configuration of the septum surface in which the slit so terminates. As a specific example, the slit 223 of FIG. 19 might thus extend from the surface 219 about midway or farther into the septum 217, and the septum would then be ruptured to extend the slit to the opposite surface 221 when a piercing member is inserted into the slit. It will therefore be understood that, when used herein, the phrase "extending at least substantially into the septum" includes the entire range of penetrations discussed, from a slit which extends at least midway through the septum, to a slit which extends entirely therethrough. It should also be recognized that it may be possible to omit the concave surfaces from the ends of the septum and still derive some benefit from the increased radially-inwardly-directed forces which are exerted on the septum when its peripheral region is compressed either by a cap or by the bonding expedient of FIG. 19.

The devices that have been illustrated are merely a few of those which may incorporate the injection site of the present invention. What has been disclosed is an injection site which will find universal utility in any medical device of the type described to which access needs to be gained by a piercing member which is either blunt or only moderately sharp, so as to prevent injury.

What is claimed is:

1. An injection site comprising:
    a housing having an inlet;
    a septum having:
        a cylindrical body having first and second opposite circular ends and a cylindrical side face extending between them;
        a concave surface in the first end of the body; and
        a slit extending axially from the concave surface at least substantially into the septum; and
    means for securing the septum to the housing at the inlet, with a peripheral portion of the septum body compressed so as to cause the concave surface to bulge, thereby becoming flat.

2. The injection site of claim 1, wherein the securing means comprises a bond between the housing and the peripheral portion of the septum.

3. The injection site of claim 1, wherein the securing means comprises a retaining cap secured to the housing, with the peripheral portion of the septum being compressed between the inlet and the cap.

4. The injection site of claim 3, wherein the cap includes an annular head with a central opening, and wherein the septum's concave surface is centered in the central opening.

5. The injection site of claim 4, wherein the cap further includes a cylindrical skirt extending axially from the cap's head, and wherein the septum is encircled by the skirt and in direct contact therewith.

6. The injection site of claim 4, wherein the external diameter of the septum exceeds the internal diameter of the skirt prior to securing the cap on the inlet.

7. The injection site of claim 4, wherein the septum body's first end face extends into the cap head's opening so that the septum body's concave surface rises substantially to the level of the cap head's exterior surface when the cap is secured to the inlet.

8. The injection site of claim 3, wherein the housing inlet includes an axially-extending cylindrical recess defined by a wall and ribs extending radially inwardly from the wall to center the septum's body within the recess.

9. The injection site of claim 8, wherein the cap further includes a cylindrical skirt extending from the cap's head, the septum is encircled by the skirt and in direct contact therewith, and the external diameter of the septum's cylindrical side face exceeds the internal diameter of the skirt prior to securing the cap to the inlet.

10. The injection site of claim 3 additionally including a second concave surface in the second end of the septum's body.

11. The injection site of claim 10, wherein the housing's inlet includes a floor with a centrally-disposed opening therein, and wherein the septum body's second end is pressed against the housing inlet's floor when the cap is secured to the inlet.

12. The injection site of claim 3, wherein the housing inlet includes a floor with a centrally-disposed opening therein, and wherein the septum body's second end is spaced from the housing inlet's floor and expands toward the floor when a piercing member is inserted through the septum's slit.

13. The injection site of claim 3, wherein the septum has a peripheral flange portion contiguous with the septum body and compressed between the inlet and the cap so as to cause the concave surface to bulge, thereby becoming flat.

14. The injection site of claim 3, wherein the inlet and the cap form opposed annular surfaces tapering away from the septum between them to create axial expansion spaces for the septum's peripheral portion.

15. The injection site of claim 1 in combination with a drug transfer spike having a piercing member extending through the septum's slit and terminating in a ball-shaped tip.

16. The injection site of claim 1, wherein the inlet forms an annular surface tapering away from the septum to create an axial expansion space for the septum's peripheral portion.

17. The injection site of claim 1, wherein the septum body extends into the housing inlet.

18. The injection site of claim 1, wherein the housing inlet terminates in a wedge-shaped rim, and the septum body is seated on that rim.

19. The injection site of claim 1 in combination with:
    a syringe having a piercing member extending through the septum slit and terminating in a ball shaped tip.

20. An injection site comprising:
    a housing having an inlet formed of a cylindrical wall including a rim;
    a septum having:
        a cylindrical body having first and second ends;
        a peripheral flange portion contiguous with the body;
        a concave surface in the first end of the body; and
        a slit extending axially from the concave surface at least substantially into the septum;
    a retaining cap having a cylindrical skirt extending from an annular, centrally-apertured head, the skirt having an internal diameter no greater than the external diameter of the septum peripheral flange portion; and
    means for securing the cap to the housing inlet wall, with the septum peripheral flange portion compressed between the cap head and the inlet rim so as to cause the septum concave surface to bulge, thereby becoming flat.

21. The injection site of claim 20, wherein the septum body first end extends beyond the septum peripheral flange portion and into the cap head central aperture so that the septum body concave surface rises within the central aperture substantially to the level of the cap head exterior surface when the cap is secured to the inlet.

22. The injection site of claim 20, wherein the housing inlet includes a floor with a centrally-disposed opening therein, the septum body additionally includes a second concave surface in its one end, and the septum body's one end is pressed against the housing inlet's floor when the cap is secured to the inlet.

23. The injection site of claim 20, wherein the housing inlet includes an axially-extending cylindrical recess defined by a wall and ribs extending radially inwardly from the wall to center the septum's body within the recess, the septum body being spaced from the wall of the inlet recess and expanding into the interstices between the wall and the ribs when a piercing member is inserted through the septum's slit.

24. A drug transfer spike comprising:
   a receptacle with an axial opening for receiving the tip of a syringe; and
   a hollow tubular piercing member in communication with the opening, the tubular piercing member terminating in a terminal portion which comprises a slanted tapered scarf which extends across opposite halves of the wall of the tubular piercing member and a tip which is ball-shaped and on the distal portion of the scarf, the radius of curvature of the tip being about one-half the dimension of the thickness of the piercing member wall.

25. An injection site comprising:
   a housing having an inlet;
   a septum having:
      a cylindrical body having first and second opposite circular end surfaces and a cylindrical side face extending between them;
      a concave surface in the first end of the body; and
      a slit extending axially from the first end concave surface through the septum; and
   a retaining cap for securing the septum to the housing at the inlet, with a peripheral portion of the septum body compressed between the inlet and the cap so as to cause the first concave end surface to bulge, thereby becoming flat, wherein the inlet forms an annular surface tapering away from the septum to create an axial expansion space for the septum peripheral portion.

26. The injection site of claim 25, wherein the septum body extends into the housing inlet.

27. The injection site of claim 25, wherein the housing inlet terminates in a wedge-shaped rim, and the septum body is seated on that rim.

* * * * *